(12) United States Patent
Sogoian

(10) Patent No.: US 6,615,791 B2
(45) Date of Patent: Sep. 9, 2003

(54) MODULAR INTERNAL COMBUSTION ENGINE

(76) Inventor: Kaloust P. Sogoian, 3019 E. Ridge Ct., Bloomfield, MI (US) 48302

(*) Notice: Subject to any disclaimer, the term of this patent is extended or adjusted under 35 U.S.C. 154(b) by 0 days.

(21) Appl. No.: 10/145,074

(22) Filed: May 14, 2002

(65) Prior Publication Data

US 2002/0170526 A1 Nov. 21, 2002

Related U.S. Application Data

(60) Provisional application No. 60/305,271, filed on Jul. 13, 2001, and provisional application No. 60/291,361, filed on May 16, 2001.

(51) Int. Cl.$^7$ .................................................. F02B 75/32
(52) U.S. Cl. .................................. 123/197.4; 123/41.84
(58) Field of Search .......................... 123/197.4, 193.3, 123/193.1, 193.2, 41.84, 41.74

(56) References Cited

U.S. PATENT DOCUMENTS

| | | | |
|---|---|---|---|
| 1,901,358 A | 3/1933 | Ryder | |
| 2,095,968 A | 10/1937 | Burgess | 123/59 |
| 2,729,117 A | 1/1956 | Maybach et al. | 74/596 |
| 4,763,619 A | 8/1988 | Eitel | 123/193 |
| 4,854,274 A * | 8/1989 | Dingess | 123/192.1 |
| 5,333,668 A | 8/1994 | Jorstad et al. | 164/100 |
| 5,452,691 A | 9/1995 | Nilsson et al. | 123/193.2 |
| 5,481,942 A | 1/1996 | Baek | 74/603 |

* cited by examiner

*Primary Examiner*—Tony M. Argenbright
*Assistant Examiner*—Katrina Harris
(74) *Attorney, Agent, or Firm*—Gifford, Krass, Groh, Sprinkle, Anderson & Citkowski, P.C.

(57) ABSTRACT

The present invention relates to a modular internal combustion engine assembly that includes a closed-dome cylinder liner having solenoid actuated intake and exhaust valves supported within the dome portion of the cylinder liner. The engine assembly also includes a crankshaft having a series of discs joined together in a spaced parallel relationship by a plurality of crankpins, that is supported at the lower end of the cylinder block by bushings adapted to receive the crankshaft, such that the crankshaft rotates within the bushings in response to piston power strokes.

15 Claims, 3 Drawing Sheets

MODULAR INTERNAL COMBUSTION ENGINE

RELATED APPLICATION

This application claims priority of U.S. Provisional Patent Application No. 60/291,361 filed May 16, 2001 and No. 60/305,271, filed Jul. 13, 2001, both of which are incorporated herein by reference.

FIELD OF THE INVENTION

This invention relates to internal combustion engines of the general type used to power vehicles and, more particularly, to a simplified compact modular engine with high reliability that can be produced at a low cost, and to components useful for such a modular engine as well as for other engine configurations.

BACKGROUND OF THE INVENTION

Automotive design and engineering will always be about options and evolution, particularly in the areas of reducing production costs and increasing fuel efficiency. The internal combustion engine is the dominant mode of power for transport in the modem world. As such, it is necessary that automotive innovators continue to improve their efficiency while reducing the cost of their production and maintenance in the interest of having a positive impact on the environment as well as the global economy.

It is the objective of the present invention to provide a modular internal combustion engine with high reliability that can be manufactured, maintained and repaired at a lower cost than conventional engines.

SUMMARY OF THE INVENTION

The present invention provides a modular internal combustion engine (ICE) assembly that includes modular components which allows for the manufacture, maintenance and repair of the present modular engine or other internal combustion engines at a lower cost.

In a preferred embodiment of the modular internal combustion engine, the assembly comprises at least one closed-dome cylinder liner, a cylinder block disposed with at least one cylinder bore adapted to receive the cylinder liner, a modular crankshaft and a plurality of bushings disposed at the lower end of the cylinder block that are adapted to support the modular crankshaft.

The closed-dome cylinder liner includes intake and exhaust valves disposed in the closed-dome portion of the cylinder liner. Preferably, these valves are solenoid actuated whereby the operation of each solenoid is handled by an engine control module. The liner is formed of an inner metallic sleeve sheathed in an aluminum casing. The inner metallic sleeve material provides the necessary porosity to fully lubricate a reciprocating piston during operation. The aluminum sheath has a shoulder portion formed adjacent the dome portion of the liner such that the dome extends above the shoulder. The shoulder portion allows the cylinder to nest on top of the cylinder block such that the shoulder and dome portion of the cylinder liner remains visible while an elongated lower portion of the liner is recessed within a cylinder bore formed in the block. To facilitate the combustion process, the dome portion of the cylinder liner is adapted to threadably receive a spark plug for the purpose of providing an ignition source to the combustion chamber and the cylinder liner is also adapted to communicate with the engine intake and exhaust manifolds as well as the fuel injection system.

As described above, the cylinder block is disposed with at least one cylinder bore adapted to receive the cylinder liner such that the shoulder portion of the liner rests on top of the cylinder block. The cylinder is fixedly mounted in place through an appropriate means known to those skilled in the art. Preferably, the cylinder bores are arranged in a staggered configuration such that the overall engine envelope is minimized.

A plurality of bushings disposed at the lower end of the cylinder block are dimensioned to support an improved crankshaft to be described hereinafter. These bushings provide a bearing and support surface within which the crankshaft rotates in response to a piston power stroke.

The improved crankshaft of the engine assembly comprises a series of discs joined together in spaced parallel relationship by a plurality of crankpins. An end disc of the crankshaft is disposed with an output shaft extending outwardly along a central axis of the crankshaft as a means of delivering mechanical power generated by the engine to peripheral components, such as gears and/or pulleys. The crankpins that connect the discs together in a spaced relationship are adapted to be connected to piston connecting rods in a journal fashion. The crankpins of the present invention serve a dual purpose as crankshaft throws and crankshaft supports commonly used in conventional crankshafts. Thus, the need for having crankshaft supports as required in conventional crankshafts is eliminated and the crankshaft's length is effectively reduced while its strength is increased.

The discs of the crankshaft are designed to have a high moment of inertia and are of an appropriate size and weight to minimize crankshaft stutter that is caused by a piston power stroke during operation. Preferably, the moment of inertia, size and weight of the discs used to construct the modular crankshaft of the present invention are such that the need for requiring a conventional flywheel is eliminated. Each disc has a circumference that is adapted to be received into the inner diameter of a bushing disposed at the lower end of the engine in a journalled fashion. As mentioned above, the bushings provide a bearing surface for the circumference of the disc much like the main bearings do for the crankshaft in a conventional engine. In response to a piston power stroke, the crankshaft rotatably moves within the bushings. The circumference of each disc may be coated with a wear-resistant material, or alternatively the bushings may provide an antifriction arrangement such as a roller or ball bearings. From the foregoing, a modular internal combustion engine may be constructed that allows for the engine envelope to be downsized without sacrificing engine output.

BRIEF DESCRIPTION OF THE DRAWINGS

To further describe the nature and objects of the present invention, reference should be had to the following detailed description taken in conjunction with the accompanying drawings in which like parts are given like reference numerals and wherein.

DETAILED DESCRIPTION OF THE INVENTION

Figure 1:
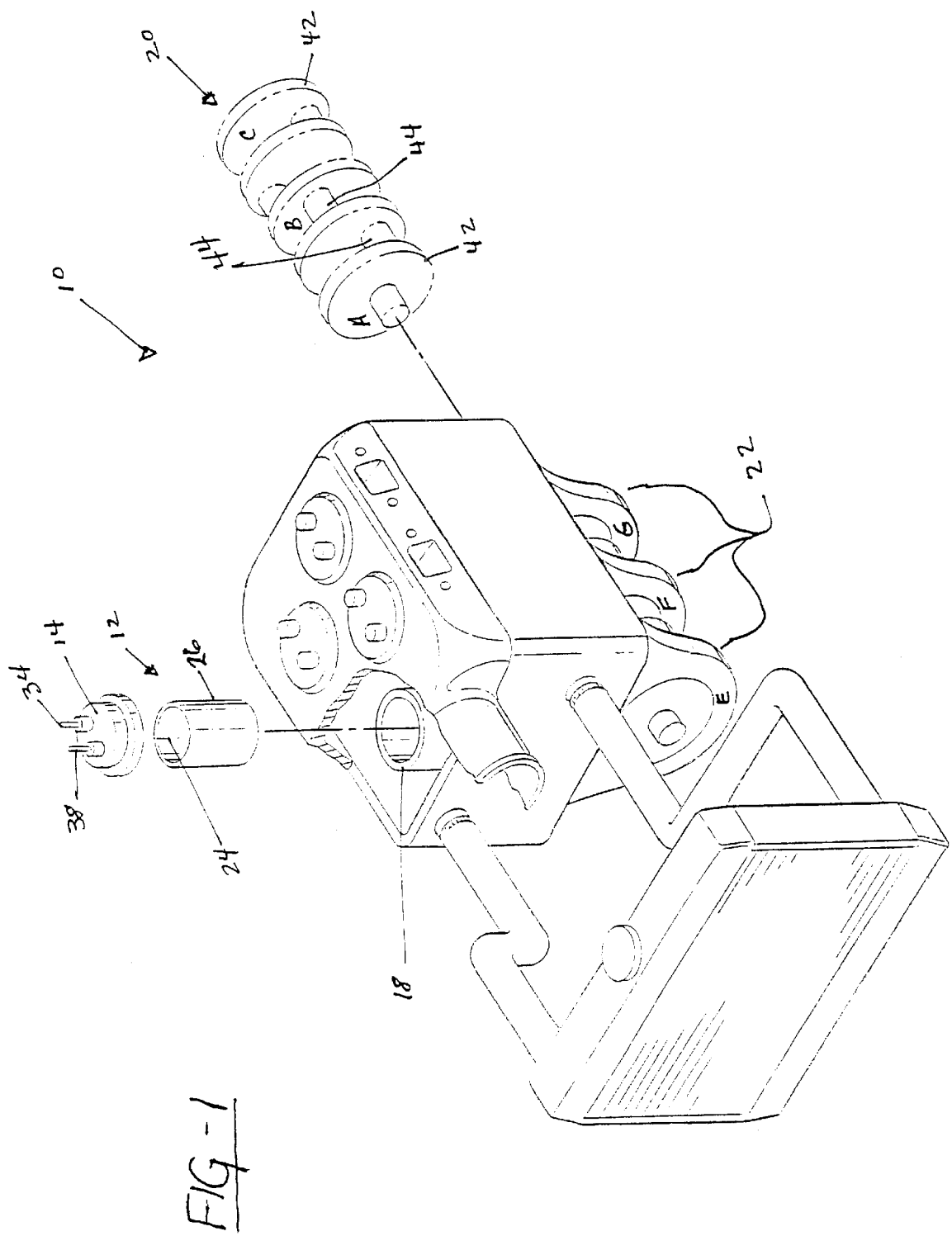
FIG. 1 is an exploded view of a modular internal combustion engine as according to the invention including cutaway portions of the cylinder block.

A preferred embodiment of the internal combustion engine assembly 10 as according to the invention is illustrated in FIG. 1 and comprises at least one closed-dome cylinder liner 12 having solenoid 15 actuated intake and exhaust valves housed within a domed portion 14, a cylinder block 16 disposed with at least one cylinder bore 18 adapted to receive the cylinder liner 12, an improved crankshaft 20 and a plurality of bushings 22 disposed at the lower end of the cylinder block adapted to receive and support the improved crankshaft 20.

Figure 3:
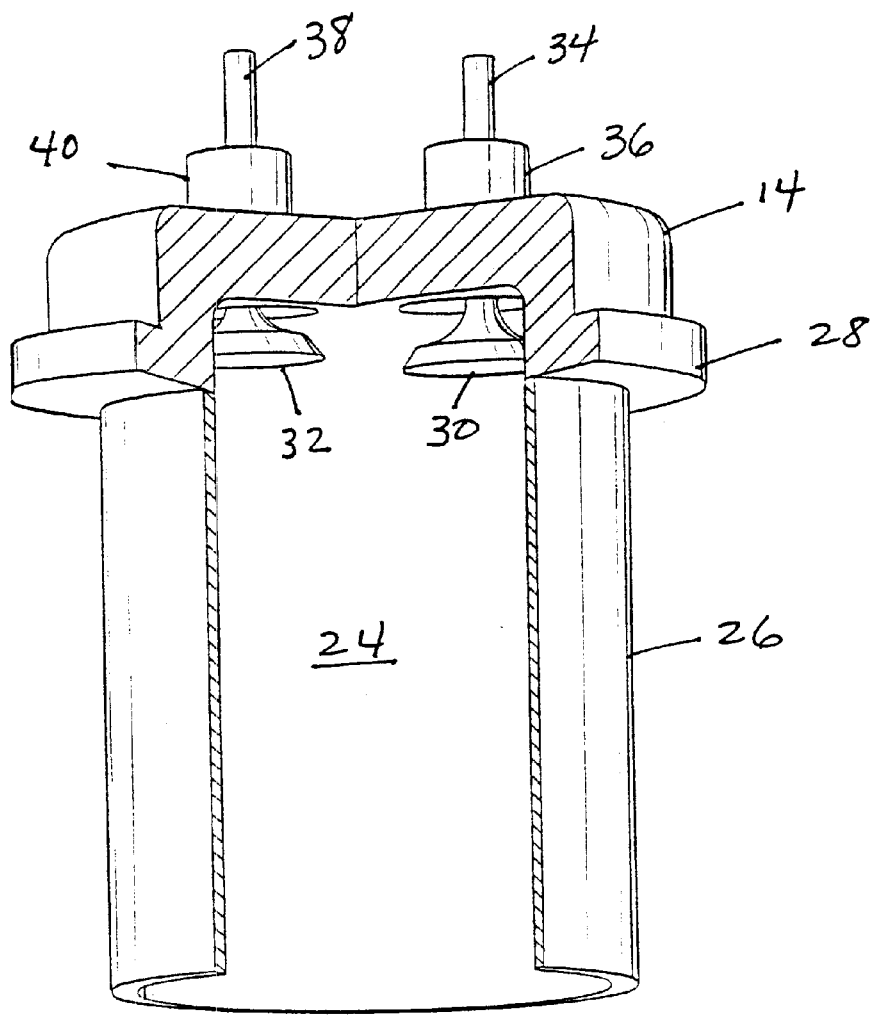
FIG. 3 is a perspective view of a cutaway of the closed-dome cylinder liner having the intake and exhaust valves supported therein as according to the invention.

As best illustrated in FIGS. 1 and 3, the closed-dome cylinder liner 12 is formed of an inner metallic sleeve 24 sheathed in an aluminum casing 26. The liner 12 includes a shoulder portion 28 extending radially from an upper end of the liner 12. Preferably, the inner sleeve 24 is cast iron and provides the necessary porosity to fully lubricate a reciprocating piston during operation. The outer aluminum casing 26 is preferably formed by impact extrusion using the machined inner sleeve as an envelope for the ram of the extrusion press. The aluminum casing 26 enhances the thermal transfer properties to a surrounding water jacket (not shown) of the cylinder block 16. Other metallic materials that provide the necessary porosity for proper lubrication of the piston may be used instead of cast iron such as aluminum. Additionally, a nonmetallic material, such as a ceramic composite, may be used to form the inner sleeve 24 as known to those skilled in the art. The cylinder liner 12 may be placed within a dry sleeve cylinder bore 18 formed in the block 16, as illustrated in FIG. 1, whereby the outer sheath of the liner is not in direct contact with the water flowing through a water jacket. Alternatively, the liner 12 may be disposed with its outer surface in direct contact with the water, sometimes referred to as a wet sleeve liner, so that the liner 12 forms one of the walls of the water jacket of the block.

Still referring to FIGS. 1 and 3, the cylinder liner 12 includes a dome portion 14 having a semi-circular shape that encloses the upper end of the casing 26. The dome portion 14 provides a support surface for an engine intake 30 and exhaust valves 32. The dome portion, or cylinder valve housing 14, extends above the shoulder 28 of the cylinder liner 12. A variety of valve arrangements may be supported in the housing, but as FIG. 3 illustrates, a single intake valve 30 and a single exhaust valve 32 are supported therein. A stem 34 of the intake valve 30 is supported in a bushing 36 that is preferably pressed into the valve housing 14. Similarly, a stem 38 of the exhaust valve 32 is supported within a bushing 40 that is preferably pressed into the cylinder valve housing 14.

Advantageously, the use of the closed-dome cylinder liner 12 within the engine assembly 10 completely eliminates the need for a separate cylinder head and accompanying cylinder head gasket. Thus, the cost of manufacture, maintenance and of repair of the engine is reduced accordingly.

It should be appreciated that the closed-dome cylinder liner 12 may be used with a conventional engine utilizing a conventional crankshaft having main bearings and an external flywheel fixed on its output shaft. Most preferably, the cylinder liner 12 is used in conjunction with other components of the modular ICE, including the improved crankshaft that will be described hereinafter. The valves of the closed-dome liner 12 are solenoid actuated. Each solenoid is precision controlled via an electronic controller associated with the engine assembly 10. Further, the dome portion 14 of the cylinder liner 12 is designed to threadably receive a spark plug (not shown) and is adapted to communicate with a fuel injection system (not shown) and engine intake and exhaust manifolds (not shown) to facilitate the combustion process.

Preferably, the cylinder block 16 is amenable to any number of cylinders in any geometric arrangement of the cylinders, such as in-line, side by side, and V, but most preferably staggered as this configuration allows the engine envelope to be significantly reduced. Each cylinder bore 18 is adapted to receive a cylinder liner 12 such that the shoulder portion 28 of the liner 12 rests on top of the cylinder block 16. The liner 12 is held in place by one of a number of ways known to those skilled in the art such as casting the liner in place, press fitting or by using an appropriate fastening means.

Figure 2:
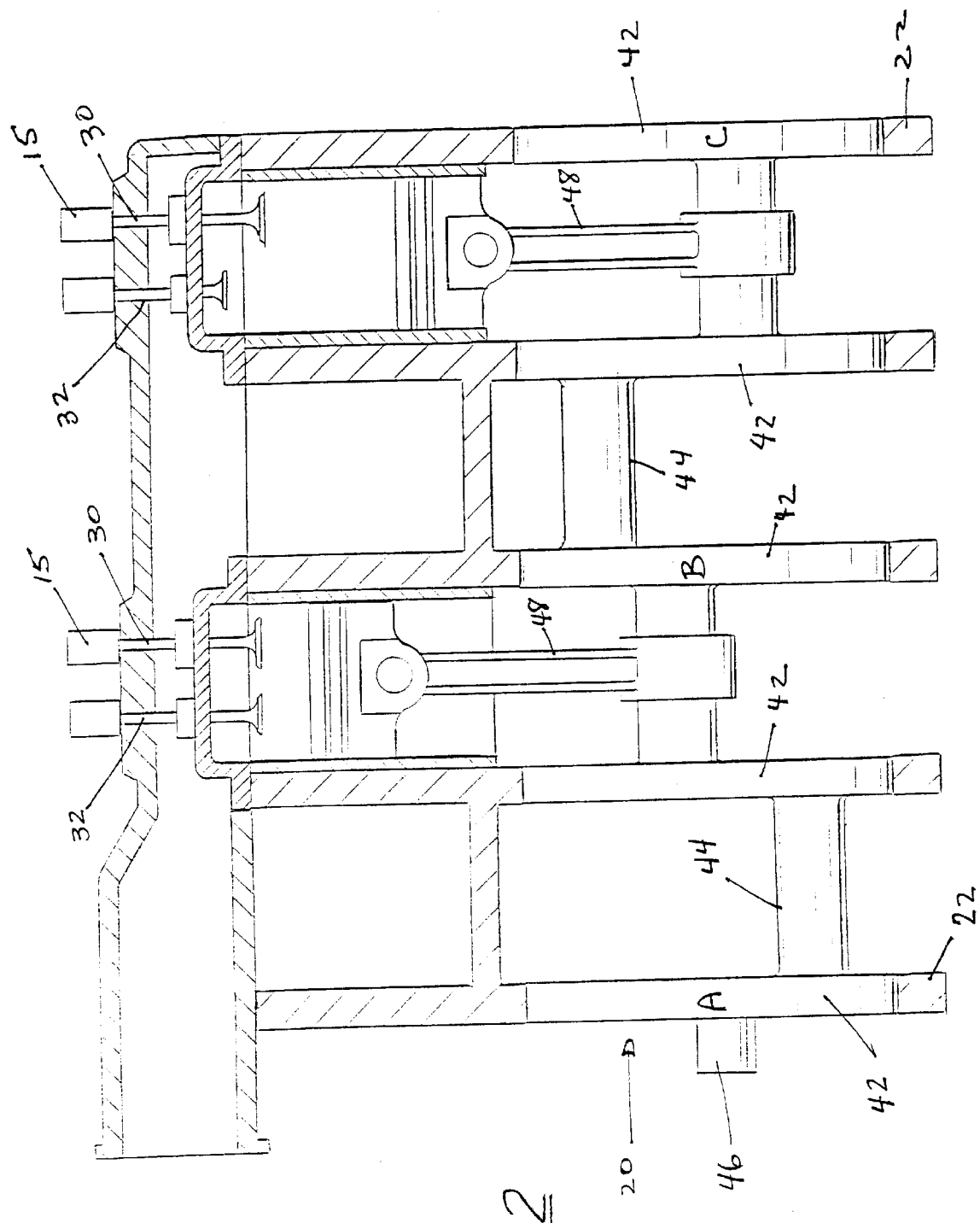
FIG. 2 is a cross-sectional view of a modular internal combustion engine as according to the invention.

Referring now to FIGS. 1 and 2, a crankshaft 20 of the engine assembly 10 includes a series of discs 42 joined together in spaced parallel relationship by a plurality of crankpins 44 with the end disc 42A, having an output shaft 46 extending outwardly along a central axis of the crankshaft 20. Each crankpin 44 that extends between the discs 42 of the crankshaft 20 is adapted to connect to a piston connecting rod 48 in a conventional manner. This replaces the need for the crankshaft throws used in conventional crankshafts. Each disc 42 has a circumference that rides within a large diameter bushing 22 formed at the lower end of the engine block 16 that will be described hereinafter.

Preferably, the size and weight of these discs 42 operates to eliminate the need for a conventional flywheel. Advantageously, the overall mass of the crankshaft 20 acts to minimize the crankshaft stutter caused by piston power strokes. The circumference of each disc 42 is preferably coated with a wear resistant friction-bearing material to eliminate the need for additional bearings. The crankshaft may be made of a single aluminum casting, or a combination of subcomponents made from various materials known to those skilled in the art. In a preferred embodiment, as described above, the modular crankshaft 20 does not require an external flywheel. Further, by eliminating the single purpose crank throws with the provision of the dual purpose crankpins 44, the overall length of the crankshaft 20 may be shortened, thus resulting in a lighter and stronger crankshaft capable of withstanding the thrust of a piston power stroke while resisting distortion.

Most preferably, the crankshaft 20 is made of a lightweight material such as aluminum. It should be apparent to those skilled in the art that a reduction in the length of the crankshaft allows for a potential reduction of the engine block envelope that may reduce engine space requirements without a proportional reduction to desired horsepower output.

As illustrated in FIGS. 1 and 2, the engine assembly 10 includes a plurality of bushings 22 positioned on a lower end of the engine block 16. The bushings are adapted to receive and support the crankshaft 20, whereby the discs 42 are supported within the bushings 22, such that the bushings 22 provide a bearing surface for the circumference of the discs 42. The crankshaft discs 42 rotate within the bushings 22 in response to piston power strokes. To enhance rotational movement, the bushings 22 may employ ball or roller bearings, or other antifriction arrangements, between the circumference of the discs 42 and the bearing surface of the bushings 22. A preferred embodiment of the engine assembly requires that discs shown at 42A, 42B and 42C of FIG. 1 are rotatably supported within the corresponding bushings 22E, 22F and 22G respectively. In this manner the two crankpins 44 positioned between discs 42A and 42B are adapted to be connected to at least one piston connecting rod 48, while the crankpins 44 between discs 42B and 42C are equally adapted to be connected to additional piston connecting rods. Preferably, the bushings 22 are made of the same material as the cylinder block, but it is understood that different materials may be made suitable for such purpose.

In an alternative embodiment, the modular ICE may include a domeless cylinder liner and a conventional cylinder head having intake and exhaust valves and being in communication with other components necessary to support the combustion process.

From the foregoing, a compact internal combustion engine 10 that includes the improved crankshaft 20 may be constructed by arranging the cylinder bores in a staggered configuration such that the engine envelope is shortened when compared to a conventional in-line internal combustion engine. It should become apparent that a compact internal combustion engine assembly 10 having an equivalent number of pistons will deliver substantially the same horsepower output as a conventional in-line engine, but from a considerably smaller package.

Components of the modular internal combustion engine may be used as replacement parts for the modular engine as well as for other conventional engine configurations. The internal combustion engine assembly 10, according to the present invention, may include at least one of the modular components described in the foregoing which includes the closed-dome cylinder liner 12, a domeless cylinder liner (not shown), or the improved crankshaft 20 as illustrated in FIG. 1 all together or in various combinations with a cylinder block and other components that are known to be necessary for the engine's proper operation by those skilled in the art.

Having thus described the invention, many modifications thereto will become apparent to those skilled in the art to which it pertains without departing from the scope and spirit of the invention as defined in the following claims.

I claim:

1. A cylinder liner for an internal combustion engine comprising:

an inner sleeve;

an outer casing surrounding said inner sleeve;

a shoulder portion extending radially from an upper end of said casing; and a dome portion having a semi-circular shape extending from said shoulder portion to enclose said upper end of said casing.

2. A cylinder liner as set forth in claim 1 wherein said inner sleeve is made of a cast iron material.

3. A cylinder liner as set forth in claim 1 wherein said outer casing is made of aluminum material.

4. A cylinder liner as set forth in claim 1 wherein said dome includes an intake valve and an exhaust valve disposed therein.

5. An internal combustion engine comprising:

a cylinder block having at least one cylinder bore;

a cylinder liner having an inner sleeve, an outer casing surrounding said inner sleeve, wherein said cylinder liner fits within the cylinder bore;

a shoulder portion extending radially from an upper end of said casing;

a dome portion having a semi-circular shape extending from said shoulder portion to enclose said upper end of said liner;

a crankshaft having a series of discs joined together in a spaced parallel relationship by a plurality of crankpins, and an end disc has an output shaft extending outwardly along a central axis, wherein said crankpins are operatively connected to piston connecting rods; and a plurality of bushings disposed at a lower end of said engine, said bushings adapted to support said crankshaft whereby the discs are received within said bushings such that the bushings provide a bearing surface for the circumference of the discs as the crankshaft rotates in response to a power stroke of the piston.

6. An engine as set forth in claim 5 wherein said crankpin serves as a crankshaft throw.

7. An engine as set forth in claim 5 wherein said inner sleeve is made of a cast iron material.

8. An engine as set forth in claim 5 wherein said outer casing is made of aluminum material.

9. An engine as set forth in claim 5 wherein said dome includes an intake valve and an exhaust valve disposed therein.

10. An engine as set forth in claim 5 wherein said disc is sheathed in a wear resistant friction-bearing material.

11. An engine as set forth in claim 5 wherein said crankshaft is made of an aluminum material.

12. An engine as set forth in claim 5 wherein said liner is a dry sleeve liner.

13. An engine as set forth in claim 5 wherein said liner is a wet sleeve liner.

14. An engine as set forth in claim 5 wherein said dome portion supports a spark plug.

15. An engine as set forth in claim 5 having a plurality of cylinder bores arranged in a staggered fashion.

* * * * *